United States Patent
Andrus et al.

(10) Patent No.: US 10,180,075 B1
(45) Date of Patent: Jan. 15, 2019

(54) ON-WING COMPONENT WEAR ANALYSIS WITH FLUID QUALITY SENSING

(71) Applicant: Rolls-Royce Corporation, Indianapolis, IN (US)

(72) Inventors: Dawn K. Andrus, Avon, IN (US); Michael T. Elliott, Westfield, IN (US); John Costello, Indianaoplis, IN (US); Anthony Fulford, Greenwood, IN (US); John Gebhard, Fishers, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 0 days.

(21) Appl. No.: 15/686,917

(22) Filed: Aug. 25, 2017

(51) Int. Cl.
  G01N 21/94 (2006.01)
  F01D 17/02 (2006.01)
  (Continued)

(52) U.S. Cl.
  CPC ............. F01D 17/02 (2013.01); F01D 25/18 (2013.01); G01N 21/94 (2013.01);
  (Continued)

(58) Field of Classification Search
  CPC ............. G01N 33/2888; G01N 11/00; G01N 21/3577; G01N 33/30; G01N 11/08; G01N 19/02; G01N 2021/3595; G01N 27/00; G01N 33/2858; G01N 15/147; G01N 15/1475; G01N 2015/1493; G01N 2015/1497; G01N 2035/1062; G01N 21/05; G01N 31/20; G01N 3/06; G01N 15/0656; G01N 15/1031; G01N 17/00; G01N 2015/1062; G01N 2015/1087; G01N 2015/1486; G01N 21/552;
  (Continued)

(56) References Cited

U.S. PATENT DOCUMENTS

| 4,599,134 A | * | 7/1986 | Babu | H05K 3/0055 |
| | | | | 134/1 |
| 4,620,185 A | * | 10/1986 | Plahmer | F16N 29/00 |
| | | | | 324/71.1 |

(Continued)

FOREIGN PATENT DOCUMENTS

RU 2420721 C1 6/2011

*Primary Examiner* — Michael P Stafira
(74) *Attorney, Agent, or Firm* — Barnes & Thornburg LLP (57) ABSTRACT

Technologies for engine fluid quality monitoring are disclosed herein. An engine system includes a gas turbine engine having one or more mechanical components, a fluid quality sensing system, and an engine controller. Each mechanical component includes a tracer material embedded in the mechanical component during manufacture. The fluid quality sensing system applies a laser beam to debris captured in an engine fluid of the gas turbine engine and detects a light signature generated by tracer material in the debris in response to application of the laser beam. The engine controller identifies the tracer material as a function of the light signature. The engine controller determines a potential wear state of a mechanical component as a function of the tracer material. The engine controller may select the mechanical component from multiple mechanical components based on the tracer material. Each mechanical component has a predetermined association with a corresponding tracer material.

20 Claims, 3 Drawing Sheets

(51) Int. Cl.
   *F01D 25/18*    (2006.01)
   *G01N 33/28*    (2006.01)
(52) U.S. Cl.
   CPC ..... *G01N 33/2888* (2013.01); *F05D 2260/98* (2013.01); *G01N 2201/06113* (2013.01)
(58) Field of Classification Search
   CPC ... G01N 2201/0221; G01N 2291/0258; G01N 2291/2695; G01N 27/07; G01N 29/036; G01N 29/222; G01N 29/46; G01N 33/28; G01N 3/068; G01N 3/56; G02B 27/62
   See application file for complete search history.

(56) References Cited

U.S. PATENT DOCUMENTS

| | | | |
|---|---|---|---|
| 4,792,791 A | 12/1988 | Cipris et al. | |
| 4,965,731 A | 1/1990 | Weitz | |
| 5,754,055 A | 5/1998 | McAdoo et al. | |
| 6,128,561 A | 10/2000 | Janata | |
| 6,463,796 B1 | 10/2002 | Van Mullekom et al. | |
| 6,553,812 B2 | 4/2003 | Park | |
| 6,794,865 B2 | 9/2004 | Astley et al. | |
| 7,184,515 B2* | 2/2007 | Wilson | G01N 23/223 378/44 |
| 7,219,536 B2 | 5/2007 | Liu et al. | |
| 7,275,418 B2 | 10/2007 | Niemann et al. | |
| 7,581,434 B1 | 9/2009 | Discenzo et al. | |
| 7,769,507 B2 | 8/2010 | Volponi et al. | |
| 7,886,875 B2 | 2/2011 | Shevchencko et al. | |
| 8,522,604 B2* | 9/2013 | Zhe | G01M 13/02 324/204 |
| 8,676,436 B2 | 3/2014 | Raimarckers et al. | |
| 9,316,630 B2 | 4/2016 | Hodgkinson et al. | |
| 9,423,392 B1 | 8/2016 | Bernhardt | |
| 9,588,097 B2* | 3/2017 | Rohde | G01N 33/2888 |
| 2002/0152985 A1 | 10/2002 | Wolff | |
| 2004/0123644 A1 | 7/2004 | Jakoby | |
| 2011/0310391 A1* | 12/2011 | Janssen | G01N 21/85 356/438 |
| 2015/0082871 A1 | 3/2015 | Zha | |
| 2016/0313237 A1 | 10/2016 | Young et al. | |
| 2018/0052104 A1* | 2/2018 | Larsson | H01J 37/32467 |

\* cited by examiner

ON-WING COMPONENT WEAR ANALYSIS WITH FLUID QUALITY SENSING

FIELD OF THE DISCLOSURE

The present disclosure relates generally to sensors and control systems used in gas turbine engine systems, and more specifically to engine oil quality monitoring.

BACKGROUND

Gas turbine propulsion systems are used to power aircraft, watercraft, power generators, and the like. A typical gas turbine propulsion system includes a gas turbine engine subsystem, an electrical power generation subsystem, a thermal management subsystem, and a lubrication subsystem.

Gas turbine engine subsystems generally include a compressor, a combustor, and a turbine. The compressor compresses air drawn into the engine and delivers high pressure air to the combustor. In the combustor, fuel is mixed with the high pressure air and is ignited. Products of the combustion reaction in the combustor are directed into the turbine where work is extracted to drive the compressor and, sometimes, an output shaft. The output shaft may drive other subsystems of the propulsion system, including the electrical power generation subsystem. Left-over products of the combustion are exhausted out of the turbine and may provide thrust in some applications. Gas turbine engines may use multiple types of engine fluids, such as lubricating oil, hydraulic fluid, fuel, and/or other engine fluids.

Typical gas turbine engines may include a magnetic chip detector to detect metallic particles in the lubricating oil. The presence of metallic particles may indicate excessive wear in one or more mechanical components of the engine. More sophisticated oil quality analysis is typically performed off-wing, in a laboratory.

SUMMARY

The present disclosure may comprise one or more of the following features and combinations thereof.

An engine system for engine fluid monitoring may include a gas turbine engine, a sump system, a fluid quality sensing system, and an engine controller. The gas turbine engine includes one or more mechanical components. Each mechanical component includes a tracer material that is embedded in the mechanical component during manufacture. The sump system is configured to capture debris from an engine fluid of the gas turbine engine. The fluid quality sensing system is configured to apply a laser beam to the debris and detect a light signature generated by the debris in response to application of the laser beam. The engine controller is configured to identify the tracer material in the debris as a function of the light signature. The tracer material generates the light signature in response to application of the laser beam. The engine controller is further configured to determine a potential wear state of the mechanical component of the gas turbine engine as a function of the tracer material. The potential wear state indicates whether the mechanical component is potentially worn or not worn.

In some embodiments, the engine fluid may include engine oil. In some embodiments, to capture the debris from the engine fluid may include to capture the debris with a magnetic chip detector. In some embodiments, to capture the debris from the engine fluid may include to capture the debris with a fluid sump.

In some embodiments, the engine controller may be further configured to log the potential wear state of the mechanical component in non-volatile storage of the engine system. In some embodiments, the engine controller may be further configured to generate a user alert based on the potential wear state of the mechanical component.

In some embodiments, to determine the potential wear state of the mechanical component may include to select the mechanical component from multiple mechanical components of the gas turbine engine based on the tracer material. Each of the mechanical components has a predetermined association with a corresponding tracer material.

According to another aspect of the present disclosure, a method for engine fluid monitoring may include capturing, by a sump system, debris from an engine fluid of the gas turbine engine; applying, by a fluid quality sensing system, a laser beam to the debris; detecting, by the fluid quality sensing system, a light signature generated by the debris in response to applying the laser beam; identifying, by an engine controller, a tracer material in the debris as a function of the light signature, wherein the tracer material generates the light signature in response to application of the laser beam; and determining, by the engine controller, a potential wear state of a mechanical component of the gas turbine engine as a function of the tracer material, wherein the tracer material is embedded in the mechanical component during manufacture, and wherein the potential wear state indicates whether the mechanical component is potentially worn or not worn.

In some embodiments, the engine fluid may include engine oil. In some embodiments, capturing the debris from the engine fluid may include capturing the debris with a magnetic chip detector. In some embodiments, capturing the debris from the engine fluid may include capturing the debris with a fluid sump.

In some embodiments, the method may further include logging, by the engine controller, the potential wear state of the mechanical component in non-volatile storage. In some embodiments, the method may further include generating, by the engine controller, a user alert based on the potential wear state of the mechanical component.

In some embodiments, wherein determining the potential wear state of the mechanical component may include selecting the mechanical component from multiple mechanical components of the gas turbine engine based on the tracer material. Each of the mechanical components has a predetermined association with a corresponding tracer material.

According to another aspect of the present disclosure, an engine controller may include tracer analysis logic to identify a tracer material in debris collected from an engine fluid of a gas turbine engine as a function of a light signature, wherein the tracer material generates the light signature in response to application of a laser beam; and determine a potential wear state of a mechanical component of the gas turbine engine as a function of the tracer material, wherein the tracer material is embedded in the mechanical component during manufacture.

In some embodiments, the engine controller may further include spectroscopy control logic to apply the laser beam to the debris in response to capturing the debris; and detect the light signature generated by the debris in response to applying the laser beam. In some embodiments, the engine fluid may include engine oil. In some embodiments, the debris may be captured from the engine fluid with a magnetic chip detector. In some embodiments, the debris may be captured from the engine fluid with a fluid sump.

In some embodiments, the tracer analysis logic may further log the potential wear state of the mechanical component in non-volatile storage of the engine controller. In some embodiments, the tracer analysis logic may further generate a user alert based on the potential wear state of the mechanical component.

In some embodiments, to determine the potential wear state of the mechanical component may include to select the mechanical component from multiple mechanical components of the gas turbine engine based on the tracer material. Each of the plurality of mechanical components has a predetermined association with a corresponding tracer material.

These and other features of the present disclosure will become more apparent from the following description of the illustrative embodiments.

DETAILED DESCRIPTION OF THE DRAWINGS

For the purposes of promoting an understanding of the principles of the disclosure, reference will now be made to a number of illustrative embodiments illustrated in the drawings and specific language will be used to describe the same.

Figure 1:
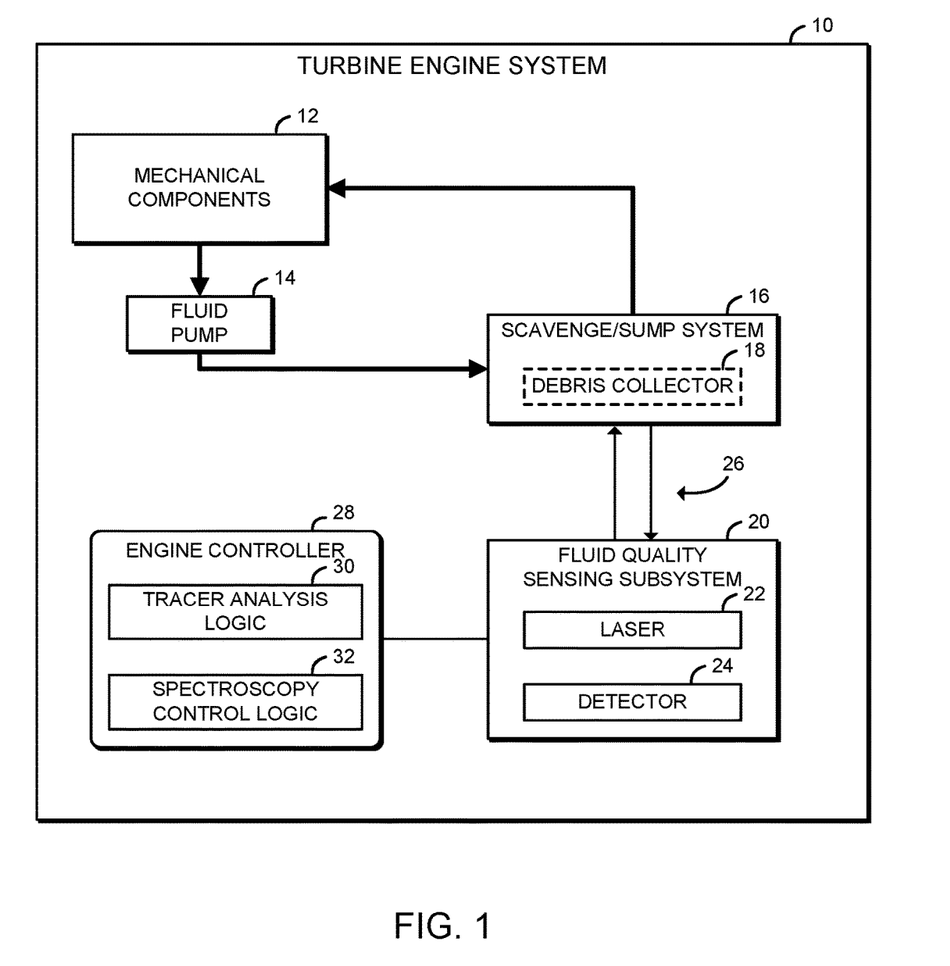
FIG. 1 is a simplified block diagram of at least one embodiment of a gas turbine engine system for a vehicle.

Referring now to FIG. 1, embodiments of a turbine engine system 10 adapted to provide thrust or power to a vehicle include mechanical components 12, a fluid pump 14, a scavenge/sump system 16, a fluid quality sensing subsystem 20, and an engine controller 28. The engine controller 28 may be embodied as any microcontroller, microprocessor, embedded system, smart sensor, or other computing device capable of performing the functions described herein. In the illustrative embodiment, in addition to various other sensing and control operations, the engine controller 28 analyzes engine fluid of the turbine engine system 10 to identify one or more of the mechanical components 12 as the source of debris in the engine fluid.

The turbine engine system 10 may be adapted to provide thrust or shaft power to an associated vehicle or system (e.g. an airplane, ship, generator, pump, or the like). In particular, the turbine engine system 10 may include a gas turbine engine including associated mechanical components 12. The mechanical components 12 may include bearings, carbon seals, shafts, and various other mechanical components of a gas turbine engine. Each mechanical component 12 may include a tracer material that embedded in the mechanical component 12 during manufacture. Each mechanical component 12 (or each type of mechanical component 12) may include a different tracer material. Each tracer material may be embodied as any material that generates an identifiable light signature when exposed to laser light, as described further below. For example, each tracer material may be embodied as a phosphor, fluorescent dye, element, or any other photoluminescent material that emits an identifiable spectrum, decay response, or other identifiable light signature in response to laser light.

The turbine engine system 10 may include one or more fluid systems that may be used to distribute and/or use various engine fluids. In particular, the turbine engine system 10 may include a lubrication system that distributes a lubricant such as oil to the mechanical components 12 of the turbine engine system 10 to provide lubrication and/or thermal management. The lubrication system may include one or more lubricant sumps, lubricant circuits, and associated lubricant pumps. The fluid pump 14 may be embodied as any oil pump, hydraulic pump, fuel pump, or other fluid pump that is configured to deliver engine fluid to the scavenge/sump system 16. The engine fluid may be pumped through the scavenge/sump system 16 to the mechanical components 12, after which the fluid is returned to the fluid pump 14 to complete a fluid circuit.

The scavenge/sump system 16 may include one or more sumps or other systems that capture engine fluid circulated through the turbine engine system 10. As shown, the scavenge/sump system 16 may include a debris collector 18 that collects debris from the fluid captured in the scavenge/sump system 16. The debris collector 18 may be embodied as a magnetic chip detector or other component to collect debris from the engine fluid. Of course, in some embodiments the scavenge/sump system 16 may collect the engine fluid without the use of a debris collector 18.

The fluid quality sensing subsystem 20 is coupled to the scavenge/sump system 16. The fluid quality sensing subsystem 20 may be embodied as any electronic sensor, smart sensor, or other sensor configured to apply laser light to debris collected from the engine fluid and detect a light signature generated by the debris in response to application of the laser light. For example, the fluid quality sensing subsystem 20 may perform laser-induced breakdown spectroscopy, fluoroscopy, or other spectrum analysis. Thus, as shown, the fluid quality sensing subsystem 20 includes a laser 22 and a detector 24 to perform those functions. Illustratively, the fluid quality sensing subsystem 20 is coupled to the scavenge/sump system 16 via a pair of fiber optic cables 26. However, in other embodiments, the fluid quality sensing subsystem 20 may be coupled to the scavenge/sump system 16 using any appropriate light transmission technique.

As shown, the fluid quality sensing subsystem 20 is communicatively coupled to the engine controller 28. The fluid quality sensing subsystem 20 and the engine controller 28 may be connected by any network interface, electrical connection, optical connection, wireless connection, or other control interface capable of transmitting sensor data and/or other information from the fluid quality sensing subsystem 20 to the engine controller 28.

The engine controller 28 may be embodied as any engine control unit, engine monitoring unit, download unit, cockpit display unit, or other computing device capable of performing the functions described herein. In some embodiments, the engine controller 28 may be embodied as a smart sensor that includes one or more sensors of the fluid quality sensing subsystem 20. In some embodiments, the engine controller 28 may be embodied as a full-authority digital engine controller (FADEC). In addition to various other sensing and control operations, the engine controller 28 may include tracer analysis logic 30 and/or spectroscopy control logic 32.

Each of the tracer analysis logic 30 and the spectroscopy control logic 32 may be embodied as hardware, firmware, software, or a combination thereof. For example, the tracer analysis logic 30 and/or the spectroscopy control logic 32 may form a portion of, or otherwise be established by, a processor or other hardware components of the engine controller 28. As such, in some embodiments, the tracer analysis logic 30 and/or the spectroscopy control logic 32 may be embodied as a circuit or collection of electrical devices (e.g., a fluid sensing logic circuit and/or a control logic circuit).

As described further below, the tracer analysis logic 30 is configured to identify a tracer material in debris collected from an engine fluid of a gas turbine engine as a function of a light signature, wherein the tracer material generates the light signature in response to application of a laser beam; and to determine a potential wear state of a mechanical component 12 of the gas turbine engine as a function of the tracer material, wherein the tracer material is embedded in the mechanical component 12 during manufacture. The tracer analysis logic 30 may be further configured to log the potential wear state of the mechanical component 12 in non-volatile storage of the engine controller 28 or to generate a user alert based on the potential wear state of the mechanical component 12. The spectroscopy control logic 32 is configured to apply the laser beam to the debris in response to capturing the debris and to detect the light signature generated by the debris in response to applying the laser beam.

Figure 2:
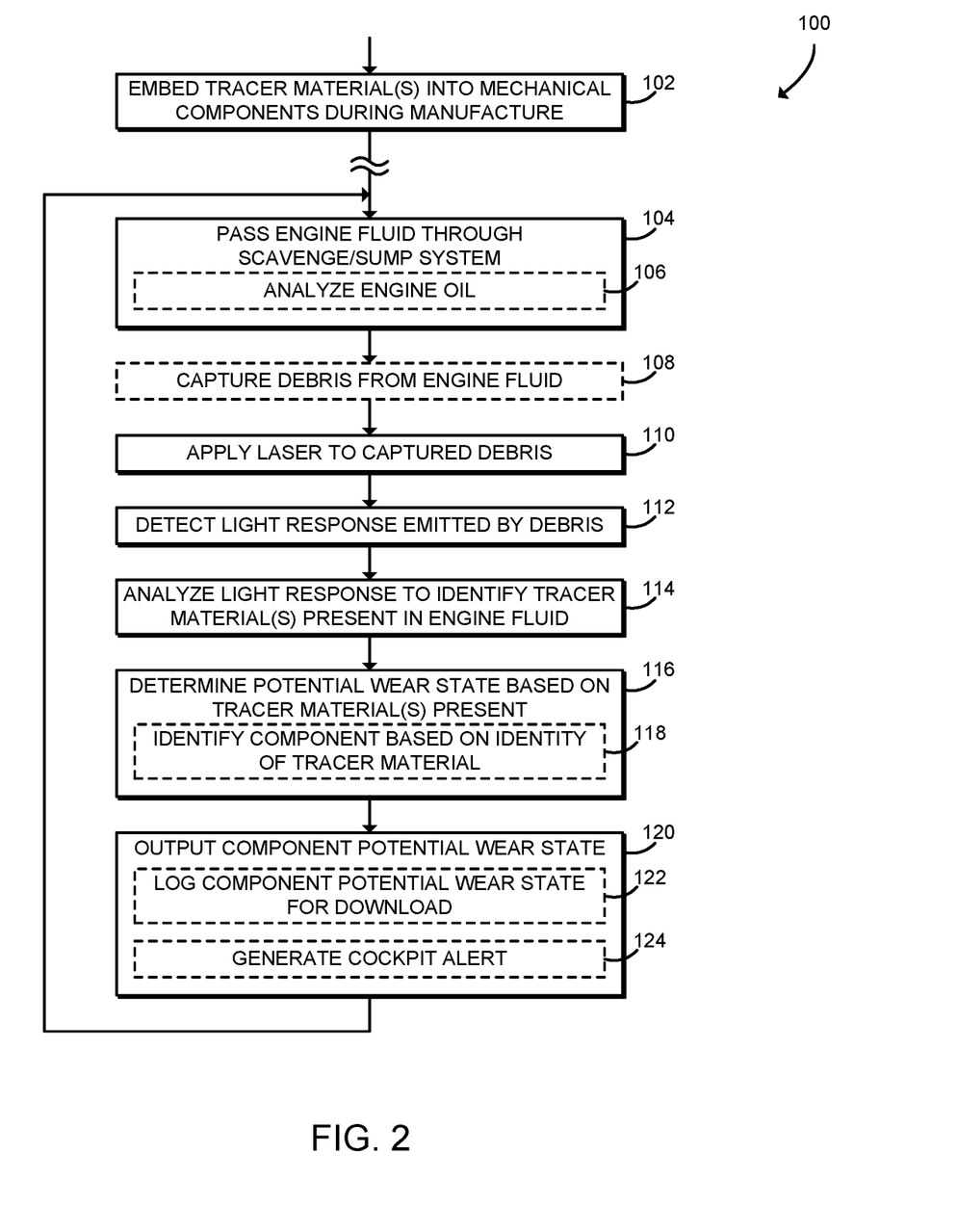
FIG. 2 is a simplified flow diagram of at least one embodiment of a method for component wear analysis that may be executed with the system of FIG. 1.

Referring now to FIG. 2, an illustrative method 100 that may be executed by the turbine engine system 10 (e.g., by the engine controller 28) is shown. Aspects of the method 100 may be embodied as electrical circuitry, computerized programs, routines, logic, and/or instructions, such as the tracer analysis logic 30 and/or the spectroscopy control logic 32. The illustrative method 100 may be executed by the turbine engine system 10 in real time during normal operation of a turbine-engine-powered vehicle/system.

The method 100 begins in block 102, in which one or more tracer materials are embedded in the mechanical components 12 of the turbine engine system 10. The tracer materials may be embedded in the mechanical components 12 during manufacture or otherwise before entering service. As described above, each tracer material may be embodied as any material that generates an identifiable light signature when exposed to laser light, as described further below. For example, each tracer material may be embodied as a phosphor, fluorescent dye, element, or any other photoluminescent material that otherwise emits an identifiable spectrum, decay response, or other identifiable light signature in response to laser light. Each mechanical component 12 or each type of mechanical components 12 may include a different tracer material. After the tracer materials are embedded in the mechanical components 12, the engine system 10 may be put into service or otherwise activated.

In block 104, while the engine system 10 is in use, an engine fluid is passed through the scavenge/sump system 16. The engine fluid may be pressurized, for example by the fluid pump 14, and passed through a fluid line or other fluid passageway to the scavenge/sump system 16. As the fluid is passed through the scavenge/sump system 16, one or more sumps may temporarily capture the engine fluid for analysis. In some embodiments, in block 106 the fluid quality sensing subsystem 20 may analyze engine oil. Additionally or alternatively, in other embodiments the fluid quality sensing subsystem 20 may analyze a different engine fluid, such as hydraulic fluid. In some embodiments, in block 108, the scavenge/sump system 16 may capture debris from the engine fluid using the debris collector 18. For example, a magnetic chip detector may collect metallic particles or other magnetic debris in the engine oil.

In block 110, the fluid quality sensing subsystem 20 applies the laser 22 to the captured debris. The laser 22 may illuminate the debris with a single wavelength of light, multiple wavelengths of light, or otherwise apply light energy to the debris. The laser light may be transmitted to the debris captured in the scavenge/sump system 16 via a fiber optic cable 26 or other light transmission medium. Illuminating the debris with laser light causes any tracer material in the debris to emit an identifiable light signature or other light response. For example, the laser may cause the tracer material to enter an excited state. The tracer material may emit light while in the excited state until the tracer material decays back to neutral. The decay rate of the emitted light may be unique to the tracer material and thus may be used to identify the presence of the tracer material.

In block 112, the fluid quality sensing subsystem 20 detects a light signature emitted by the debris using the detector 24. In particular, the detector 24 may determine the wavelength(s) of light, intensity of light, rate of decay of light, or other light response emitted by the debris in response to application of the laser 22. The light signature may be transmitted from the debris in the fluid capture sump via a fiber optic cable 26 or other light transmission medium. After measuring the light signature, the fluid quality sensing subsystem 20 may provide a decay signal, measurement signal, or other sensor data to the engine controller 28. For example, the light signature data may be transmitted via a direct connection, a vehicle network, a wireless connection, or other data connection to the engine controller 28. Of course, in some embodiments the engine controller 28 and the fluid quality sensing subsystem 20 may be integrated, for example as a smart sensor. In those embodiments, the engine controller 28 may analyze the light signature data and then provide processed results to another controller of the turbine engine system 10.

In block 114, the engine controller 28 analyzes the light signature received by the detector 24 to identify any tracer materials in the debris. The engine controller 28 may, for example, identify one or more tracer materials based on the rate of decay of the light response generated by the debris. As another example, the engine controller 28 may identify one or more tracer materials based on a light spectrum or other light signature generated by the debris.

In block 116, the engine controller 28 determines a potential wear state (e.g., potentially worn or not worn) for the mechanical components 12 based on the identified tracer materials. The presence of tracer materials in the engine fluid indicates that the associated mechanical component 12 may be worn, causing particles to enter the engine fluid. Thus, the engine controller 28 may identify the mechanical components 12 as potentially worn or not worn based on the presence of tracer materials in the engine fluid. In some embodiments, in block 118 the engine controller 28 may identify the potentially worn mechanical components 12 based on the identity of the detected tracer materials. For example, the engine controller 28 may include a database or other predetermined data structure that defines associations between tracer materials and corresponding mechanical components 12 and/or types of mechanical components 12.

In block 120, the engine controller 28 outputs the mechanical component 12 potential wear state. The engine controller 28 may use any appropriate technique to output the potential wear state, such as presenting the potential wear state with one or more displays, storing the potential wear state in data storage, transmitting the potential wear state to another controller or other computing device of the engine system 10, or otherwise using the determined potential wear state. In some embodiments, in block 122 the engine controller 28 may log the potential wear state for later download. For example, the engine controller 28 (or another computing device in communication with the engine controller 28) may store the potential wear state in non-volatile data storage. The logged potential wear state may be later downloaded and analyzed, for example when performing vehicle maintenance. In some embodiments, in block 124 the engine controller 28 may generate a cockpit alert based on the potential wear state. For example, the engine controller 28 (or another computing device in communication with the engine controller 28) may generate an alert to the cockpit to identify potential required maintenance based on the potential wear state. After outputting the determined potential wear state, the method 100 loops back to block 104 to continue performing wear analysis.

Figure 3:
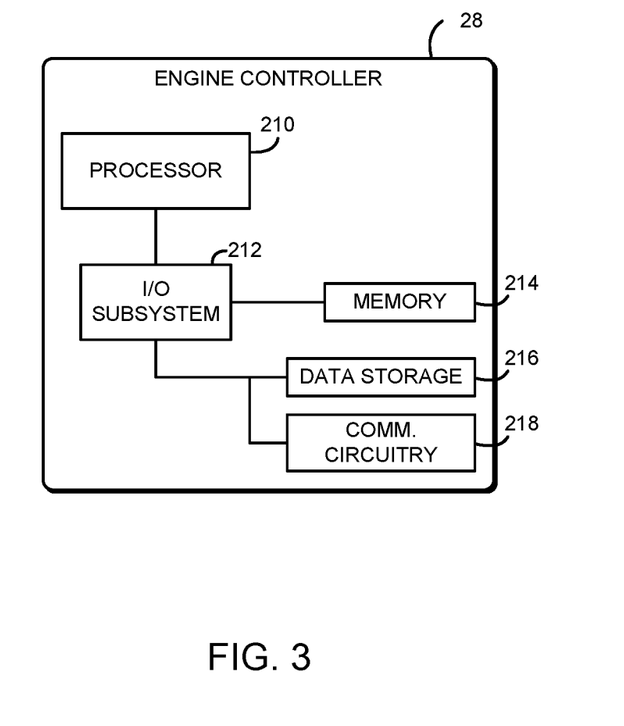
FIG. 3 is a simplified block diagram of at least one embodiment of an engine controller of FIG. 1.

Referring now to FIG. 3, an embodiment of the engine controller 28 is shown. The illustrative engine controller 28 is embodied as one or more computing devices, which may include one or more controllers or processors (e.g., microcontrollers, microprocessors, digital signal processors, field-programmable gate arrays (FPGAs), programmable logic arrays (PLAs), etc.), and/or other electrical circuitry. The engine controller 28 includes hardware, firmware, and/or software components that are capable of performing the functions disclosed herein, including the functions of the tracer analysis logic 30 and/or the spectroscopy control logic 32. The engine controller 28 may be in communication with one or more other devices (such as one or more embedded controllers) by one or more communication networks (not shown), in order to perform one or more of the disclosed functions. Additionally, although illustrated as a single component, it should be understood that in some embodiments the functions of the engine controller 28 may be distributed in multiple components through the turbine engine system 10.

The illustrative engine controller 28 includes at least one processor 210, an input/output (I/O) subsystem 212, and a memory 214. The I/O subsystem 212 typically includes, among other things, an I/O controller, a memory controller, and one or more I/O ports, although not specifically shown. The processor 210 and the I/O subsystem 212 are communicatively coupled to the memory 214. The memory 214 may be embodied as any type of suitable computer memory device (e.g., volatile memory such as various forms of random access memory). The I/O subsystem 212 is communicatively coupled to a number of hardware and/or software components, including a data storage device 216 and communication circuitry 218.

The data storage device 216 may include one or more hard drives or other suitable persistent data storage devices (e.g., flash memory, memory cards, memory sticks, read-only memory devices, and/or others). Information about the different operating conditions of the turbine engine system 10, and/or any other data needed by the turbine engine system 10 (e.g., the tracer analysis logic 30 and/or the spectroscopy control logic 32) may be stored in the data storage device 216. Portions of the tracer analysis logic 30 and/or the spectroscopy control logic 32 may be copied to the memory 214 during operation of the turbine engine system 10, for faster processing or other reasons. The tracer analysis logic 30 and the spectroscopy control logic 32 are embodied as one or more computer-executable components and/or data structures (e.g., computer hardware, firmware, software, or a combination thereof). Particular aspects of the methods that may be performed by the tracer analysis logic 30 and/or the spectroscopy control logic 32 may vary depending on the requirements of a particular design of the turbine engine system 10. Accordingly, the examples described herein are illustrative and intended to be non-limiting.

The communication circuitry 218 may communicatively couple the engine controller 28 to one or more other devices, systems, or communication networks, e.g., a vehicle area network, controller area network, local area network, and/or wide area network, for example. Accordingly, the communication circuitry 218 may include one or more wired or wireless network interface software, firmware, or hardware, for example, as may be needed pursuant to the specifications and/or design of the particular turbine engine system 10. Further, the engine controller 28 may include other components, sub-components, and devices not illustrated herein for clarity of the description. In general, the components of the engine controller 28 are communicatively coupled as shown in FIG. 3 by electronic signal paths, which may be embodied as any type of wired or wireless signal paths capable of facilitating communication between the respective devices and components.

In the foregoing description, numerous specific details, examples, and scenarios are set forth in order to provide a more thorough understanding of the present disclosure. It will be appreciated, however, that embodiments of the disclosure may be practiced without such specific details. Further, such examples and scenarios are provided for illustration, and are not intended to limit the disclosure in any way. Those of ordinary skill in the art, with the included descriptions, should be able to implement appropriate functionality without undue experimentation.

References in the specification to "an embodiment," etc., indicate that the embodiment described may include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to effect such feature, structure, or characteristic in connection with other embodiments whether or not explicitly indicated.

Embodiments in accordance with the disclosure may be implemented in hardware, firmware, software, or any combination thereof. Embodiments may also be implemented as instructions stored using one or more machine-readable media, which may be read and executed by one or more processors. A machine-readable medium may include any mechanism for storing or transmitting information in a form readable by a machine. For example, a machine-readable medium may include any suitable form of volatile or non-volatile memory.

Modules, data structures, and the like defined herein are defined as such for ease of discussion, and are not intended to imply that any specific implementation details are required. For example, any of the described modules and/or data structures may be combined or divided into sub-modules, sub-processes or other units of computer code or data as may be required by a particular design or implementation.

In the drawings, specific arrangements or orderings of schematic elements may be shown for ease of description. However, the specific ordering or arrangement of such elements is not meant to imply that a particular order or sequence of processing, or separation of processes, is required in all embodiments. In general, schematic elements used to represent instruction blocks or modules may be implemented using any suitable form of machine-readable instruction, and each such instruction may be implemented using any suitable programming language, library, application programming interface (API), and/or other software development tools or frameworks. Similarly, schematic elements used to represent data or information may be implemented using any suitable electronic arrangement or data structure. Further, some connections, relationships, or associations between elements may be simplified or not shown in the drawings so as not to obscure the disclosure.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

The invention claimed is:

1. An engine system for engine fluid monitoring, the engine system comprising:
   a gas turbine engine that comprises a mechanical component, wherein the mechanical component includes a tracer material that is embedded in the mechanical component during manufacture;
   a sump system to capture debris from an engine fluid of the gas turbine engine;
   a fluid quality sensing system to (i) apply a laser beam to the debris and (ii) detect a light signature generated by the debris in response to application of the laser beam; and
   an engine controller to (i) identify the tracer material in the debris as a function of the light signature, wherein the tracer material generates the light signature in response to application of the laser beam, and (ii) determine a potential wear state of the mechanical component of the gas turbine engine as a function of the tracer material, wherein the potential wear state indicates whether the mechanical component is potentially worn or not worn.

2. The engine system of claim 1, wherein the engine fluid comprises engine oil.

3. The engine system of claim 1, wherein to capture the debris from the engine fluid comprises to capture the debris with a magnetic chip detector.

4. The engine system of claim 1, wherein to capture the debris from the engine fluid comprises to capture the debris with a fluid sump.

5. The engine system of claim 1, wherein the engine controller is further to log the potential wear state of the mechanical component in non-volatile storage of the engine system.

6. The engine system of claim 1, wherein the engine controller is further to generate a user alert based on the potential wear state of the mechanical component.

7. The engine system of claim 1, wherein to determine the potential wear state of the mechanical component comprises to select the mechanical component from a plurality of mechanical components of the gas turbine engine based on the tracer material, wherein each of the plurality of mechanical components has a predetermined association with a corresponding tracer material.

8. A method for engine fluid monitoring, the method comprising:
   capturing, by a sump system, debris from an engine fluid of the gas turbine engine;
   applying, by a fluid quality sensing system, a laser beam to the debris;
   detecting, by the fluid quality sensing system, a light signature generated by the debris in response to applying the laser beam;
   identifying, by an engine controller, a tracer material in the debris as a function of the light signature, wherein the tracer material generates the light signature in response to application of the laser beam; and
   determining, by the engine controller, a potential wear state of a mechanical component of the gas turbine engine as a function of the tracer material, wherein the tracer material is embedded in the mechanical component during manufacture, and wherein the potential wear state indicates whether the mechanical component is potentially worn or not worn.

9. The method of claim 8, wherein the engine fluid comprises engine oil.

10. The method of claim 8, wherein capturing the debris from the engine fluid comprises capturing the debris with a magnetic chip detector.

11. The method of claim 8, wherein capturing the debris from the engine fluid comprises capturing the debris with a fluid sump.

12. The method of claim 8, further comprising logging, by the engine controller, the potential wear state of the mechanical component in non-volatile storage.

13. The method of claim 8, further comprising generating, by the engine controller, a user alert based on the potential wear state of the mechanical component.

14. The method of claim 8, wherein determining the potential wear state of the mechanical component comprises selecting the mechanical component from a plurality of mechanical components of the gas turbine engine based on the tracer material, wherein each of the plurality of mechanical components has a predetermined association with a corresponding tracer material.

15. An engine controller comprising tracer analysis logic to:
   identify a tracer material in debris collected from an engine fluid of a gas turbine engine as a function of a light signature, wherein the tracer material generates the light signature in response to application of a laser beam; and
   determine a potential wear state of a mechanical component of the gas turbine engine as a function of the tracer material, wherein the tracer material is embedded in the mechanical component during manufacture.

16. The engine controller of claim 15, further comprising spectroscopy control logic to:
   apply the laser beam to the debris in response to capturing the debris; and
   detect the light signature generated by the debris in response to applying the laser beam.

17. The engine controller of claim 15, wherein the engine fluid comprises engine oil.

18. The engine controller of claim 15, wherein the tracer analysis logic is further to log the potential wear state of the mechanical component in non-volatile storage of the engine controller.

19. The engine controller of claim 15, wherein the tracer analysis logic is further to generate a user alert based on the potential wear state of the mechanical component.

20. The engine controller of claim 15, wherein to determine the potential wear state of the mechanical component comprises to select the mechanical component from a plurality of mechanical components of the gas turbine engine based on the tracer material, wherein each of the plurality of mechanical components has a predetermined association with a corresponding tracer material.

\* \* \* \* \*